United States Patent [19]

Thomas et al.

[11] Patent Number: 5,099,083
[45] Date of Patent: Mar. 24, 1992

[54] PROCESS FOR PREPARING 3-CHLOROMETHYLBENZO-CYCLOBUTENE

[75] Inventors: P. J. Thomas; R. Garth Pews, both of Midland, Mich.

[73] Assignee: The Dow Chemical Company, Midland, Mich.

[21] Appl. No.: 655,872

[22] Filed: Feb. 14, 1991

[51] Int. Cl.⁵ .................. C07C 17/00; C07C 17/08
[52] U.S. Cl. ........................... 570/194; 570/191
[58] Field of Search .................. 570/191, 194

[56] References Cited

U.S. PATENT DOCUMENTS

| | | | |
|---|---|---|---|
| 1,910,475 | 5/1933 | Reddelien et al. | 570/194 |
| 2,212,099 | 8/1940 | Jones | 570/194 |
| 2,219,873 | 10/1940 | Pinkernelle | 570/194 |
| 2,780,604 | 2/1957 | Clark et al. | 570/194 |
| 2,846,480 | 8/1958 | Mc Claflin et al. | 570/194 |
| 2,889,377 | 6/1959 | Floria | 570/194 |
| 3,076,039 | 1/1963 | Ayers et al. | 570/194 |
| 3,284,518 | 11/1966 | Ayers et al. | 570/191 |
| 3,297,648 | 1/1967 | Corte et al. | 570/194 |
| 3,311,602 | 3/1967 | Raley, Jr. | 570/194 |
| 4,562,280 | 12/1985 | Gilpin et al. | 570/194 |

OTHER PUBLICATIONS

Ewing et al., "Novel Synthesis of [2.2.2] (1,2,4) Cyclophane", *J.C.S. Chem. Comm.*, 1979, pp. 207–208.
Fuson et al., *Organic Reactions*, vol. 1, pp. 68–69.

*Primary Examiner*—Werren B. Lone
*Attorney, Agent, or Firm*—Charles J. Enright; John A. Gazewood

[57] ABSTRACT

3-chloromethylbenzocyclobutene is prepared by reacting benzocyclobutene with chloromethyl methyl ether in the presence of stannic chloride at a temperature of about −120° C. to about −40° C. and neutralizing the resulting reaction mixture comprising 3-chloromethylbenzocyclobutene at a temperature of about −80° C. to about −70° C.

17 Claims, No Drawings

PROCESS FOR PREPARING 3-CHLOROMETHYLBENZO-CYCLOBUTENE

BACKGROUND OF THE INVENTION

The present invention relates to the process for the preparation of 3-chloromethylarylcyclobutene compounds.

In recent years, the search for high-performance materials, especially high temperature-resistant polymers, has gained momentum. In order for polymeric materials to have stability at high temperatures, they must fulfill several requirements, including high melting or softening temperatures, high modulus or rigidity, a resistance to solvent and chemical degradation and toughness. The intrinsic thermal and oxidative stability of aromatic structures has long been recognized, and a variety of polymers have been made in which benzene rings ar linked together by various connecting groups.

Aromatic hydrocarbons which have cyclobutene rings fused to the aromatic nucleus are useful in the preparation of high-performance polymers. These high-performance polymers exhibit thermal stability at elevated temperatures, chemical resistance to most conventional solvents, good mechanical and electrical properties, and low sensitivity to water. They are useful as films, advanced composites, adhesives, structural laminates, matrix resins, and planarization resins for the electronics and aerospace industries.

The cyclobutene-substituted aromatic hydrocarbons are also suitable for preparing aromatic ring-substituted intermediates which are themselves polymerizable or can be used to introduce the arylcyclobutene moiety into a variety of monomers and polymers to enhance heat resistance of the ultimate products. It is, however, quite difficult to introduce reactive groups into the aromatic nucleus of arylcyclobutene compounds because severe reaction conditions which are often required for such nuclear substitutions can result in an undesired opening of the cyclobutene ring. In addition, yields of the desired product are often too low for commercial acceptability.

Haloalkylated derivatives, particularly halomethylated derivatives, of aromatic organic compounds are a particularly desirable intermediate because the chloromethyl or bromomethyl group can be easily converted to other groups such as —COOH, —CH$_2$OH, —CHO, —CH$_2$CN and —CH$_3$. The chloromethylation of aromatic compounds is a well-known reaction. The chloromethylation of aromatic compounds involves the replacement of a hydrogen atom on the cyclic nucleus of an aromatic ring by a chloromethyl group in a single operation. The reaction typically proceeds at temperatures in the rang from 0° to 120° C. under acidic conditions. Thus, aromatic and alkaryl hydrocarbons have been chloromethylated by treatment with formaldehyde and hydrochloric acid; paraformaldehyde, zinc chloride, and hydrogen chloride; or paraformaldehyde, concentrated sulfuric acid, and hydrogen chloride.

Other effective chloromethylating reagents include E,E'-bischloromethyl ether and monochloromethyl methyl ether. The reaction is typically carried out in the presence of zinc chloride, stannous chloride, stannic chloride, aluminum trichloride, boron trifluoride, ferric chloride, titanium tetrachloride, as well as protic acids such as hydrogen chloride (taken in excess and behaving simultaneously as a reactant), sulfuric acid, phosphoric acid, chlorosulfonic acid and acetic acid. Zinc chloride is used most frequently, generally with a small amount of aluminum chloride to increase its activity. For example, 2,4,6-triisopropylbenzyl chloride is prepared by reacting chloromethyl ether with 1,3,5-triisopropylbenzene in the presence of stannic chloride at 0° C.

Gilpin et al U.S. Pat. No. 4,562,280 disclose the chloromethylation of deactivated aromatic compounds which comprises contacting an aromatic compound substituted with an alkyl group and a deactivating group with a chloromethyl alkyl ether in an inert organic reaction medium in the presence of a catalytic amount of ferric chloride or stannic substituted with an alkyl group, a chloromethyl group and a deactivating group, wherein the alkyl and chloromethyl groups are on adjacent carbon atoms, is prepared. Generally, the Gilpin et al process is run at temperatures between about 40° C. and 80° C.

Attempts to chloromethylate arylcyclobutene compound at the known prior art conditions have been relatively unsuccessful because of the tendency of the cyclobutene ring which is fused to the aromatic nucleus to open under acidic conditions even at relatively mild temperatures, resulting in little, if any, yield of the desired chloromethylarylcyclobutene product. 4-chloromethylbenzocyclobutene has been prepared by the pyrolysis of 2,4-bis(chloromethyl)toluene in the gas phase at 700° C., Ewing et al "Novel Syntheses of [2.2.2] (1,2,4) Cyclophane", *J.C.S. Chem. Comm.*, 1979, pages 207–208.

SUMMARY OF THE INVENTION

In accordance with the present invention, there is provided a process for the chloromethylation of arylcyclobutene compounds which comprises reacting at a temperature in the range from about −120° C. to about −40° C., at least one arylcyclobutene compound with an excess of chloromethyl methyl ether in the presence of stannic chloride and neutralizing the reaction mixture comprising chloromethylarylcyclobutene at a temperature in the range of about −80° C. to about −70° C. Preferably, the neutralizing agent will be at a temperature of 0° C. or lower prior to its being added to the reaction mixture containing the chloromethylarylcyclobutene product.

DESCRIPTION OF THE PREFERRED EMBODIMENT

The arylcyclobutene moiety can be any aromatic radical which has at least one cyclobutene ring fused to at least one of the aromatic rings. The term "aryl" refers herein to any aromatic radical. "Aromatic" as used herein refers to carbocyclic or heterocyclic rings in which (4n+2) delocalized pi electrons are contained in an orbital ring, as described in Morrison and Boyd, *Organic Chemistry*, 3d ed., 1973. This property is also known as "resonance stabilization" or "delocalization". Preferred carbocyclic aromatic radicals include benzene, naphthalene, phenanthrene, anthracene, pyridine, biaryl moieties, or two or more aromatic radicals bridged by alkylene or cycloalkylene moieties. More preferred carbocyclic radicals include benzene, naphthalene, biphenyl, binaphthyl, or a diphenyl alkylene or a diphenyl cycloalkylene compound. The preferred carbocyclic aromatic radical is benzene. Examples of preferred heterocyclic radicals include pyrrole, furan, thiophene, imidazole, oxazole, thiazole, pyrazole, pyridine and pyrimidine. More preferred heterocyclic aromatic rings are pyridine, furan and thiophene, with pyridine being most preferred. The carbocyclic aromatic rings are preferred over the heterocyclic aromatic rings. Except for the fused butene ring, the aromatic nucleus is unsubstituted.

Arylcyclobutene compounds which are converted to the corresponding chloromethylarylcyclobutene in accordance with the invention correspond to the formula:

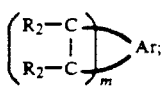

wherein Ar is an aryl moiety; R is separately and independently in each occurrence hydrogen, an electron-donating moiety or an electron-withdrawing moiety; and m in an integer of at least 1. "Separately and independently in each occurrence" means that R can be the same or different in each occurrence.

The cyclobutene ring or rings may be substituted with electron-withdrawing groups or electron-donating groups. Electron-donating moieties are molecular or nucleus groups which donate electrons more than a hydrogen atom would if accompanying the same site. Electron-withdrawing moieties are groups which more readily withdraw an electron relative to a hydrogen atom. Examples of suitable electron-withdrawing moieties include $-NO_2$, $-CN$, Br, I, Cl, F, $-PR_2$, $-CO_2H$, $-CO_2R$, $-C(O)R$, $-C(O)$-aryl, $-S(O)-R$, $-S(O)$-aryl, $-SO_2-R$ and aryl. Examples of suitable electron-donating groups include alkyl, aryl, alcoxy, aryloxy, hydrocarbyl, hydrocarbyloxy, hydrocarbylthio, $-OH$, $-OR$, $-NH_2$, $-NHR$ and $-NR_2$. Hydrocarbyl refers to any organic moiety containing carbon and hydrogen atoms; hydrocarbyloxy refers to such organic moieties which further contain a hydroxyl moiety; and hydrocarbylthio refers to organic moieties which further contain a sulfur atom. Preferred substituents on the cyclobutene ring are cyano, carboxylate, hydrocarbylcarbonyloxy, nitro, halo and hydrocarbylthio. More preferred substituents include halo, nitro or cyano groups, with cyano groups being most preferred.

The most preferred arylcyclobutene compound is benzocyclobutene having the formula:

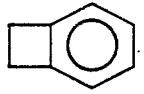

The preferred benzocyclobutene is readily prepared by the pyrolysis of 2-chloromethyl-1-methylbenzene in an inert solvent such as o-xylene at a temperature in the range of 700° -750° C. An alternate method of forming benzocyclobutene is described in Quaderer U.S. Pat. No. 4,851,603 in which 2-chloromethyl-1-methylbenzene is dehydrohalogenated in the presence of steam to form benzocyclobutene.

The chloromethyl methyl ether is a well-known article of commerce. It can be prepared by mixing paraformaldehyde with methanol and cooling the mixture to about 0° C. A rapid stream of hydrogen chloride is passed through the mass until two layers form and all the paraformaldehyde has disappeared. It is necessary to keep the mixture cool to prevent the formation of methylal. The upper layer is then separated, dried over calcium chloride and fractionated several times. The chloromethyl methyl ether boils at 57° -59° C. and is about 90% pure. By washing with concentrated hydrochloric acid, it is possible to obtain a product which is 95% chloromethyl methyl ether.

While the invention is broadly applicable to the chloromethylation of substantially any arylcyclobutene compound, the invention will be specifically described with respect to the preferred embodiment, that is, the chloromethylation of benzocyclobutene to 3-chloromethylbenzocyclobutene. The most precise nomenclature for this compound appears to be 3-chloromethyl, bicyclo[4.2.0]-octa-1,3,5-triene. These terms may be used interchangeably to refer to the same compound.

In the process of this invention, benzocyclobutene is reacted with chloromethyl methyl ether, preferably in the presence of an inert organic reaction medium, at a temperature in the range from about $-120°$ C. to about $-40°$ C., and preferably about $-80°$ C. to about $-70°$ C., whereby the benzocyclobutene is converted to 3-chloromethylbenzocyclobutene (3-chloromethyl, bicyclo[4.2.0]-octa-1,3,5-triene):

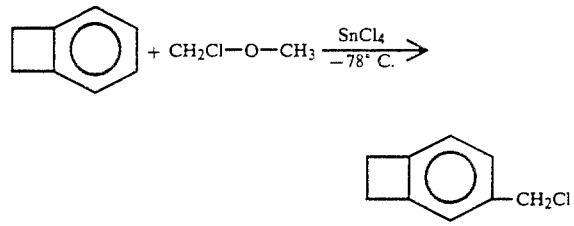

The crude reaction product is subsequently neutralized with a neutralization agent which has been cooled to at least 0° C., at the reaction temperature, and preferably in the range from about $-80°$ C. to about $-70°$ C. Substantially any neutralizing agent, such as ammonium hydroxide or sodium hydroxide can be employed to neutralize the 4-chloromethylbenzocyclobutene reaction product, with sodium hydroxide being currently preferred. Excessive temperature should be avoided because of the tendency of the 4-chloromethylbenzocyclobutene to undergo an opening of the cyclobutene ring at temperatures of $-20°$ C. and higher in the presence of an acidic medium, such as hydrochloric acid which forms as a reaction by-product. The reaction is preferably effected in the presence of organic solvents which are inert with respect to the reactants. Suitable solvents include ethylene dichloride, methyl cyanide and methylene dichloride, with methylene dichloride being a preferred solvent. Typically, at least stoichiometric quantities of benzocyclobutene and chloromethyl methyl ether are employed. However, it is currently preferred to conduct the chloromethylation reaction using a stoichiometric excess of chloromethyl methyl ether.

It has been found that stannic chloride is effective to catalyze the chloromethylation of benzocyclobutene to 3-chloromethylbenzocyclobutene. The stannic chloride is employed in catalytic amounts, most preferably about 0.5 moles/mole benzocyclobutene Following the chloromethylation reaction, the reaction mixture is maintained at about $-78°$ C. and excessive acidity is neutralized, for example, by adding a base such as sodium carbonate, ammonium hydroxide or sodium hydroxide with the latter being particularly preferred. The neutralization agent is preferably cooled to at least 0° C. prior to its addition to the reaction medium. After neutralizing with the ice cold sodium hydroxide solution, it is extracted with ethyl acetate. The organic layer is then washed with brine and dried over anhydrous magnesium sulfate. Removal of the solvent followed by purification by flash chromatography results in recovery of 3-chloromethylbenzocyclobutene as a colorless liquid. The process may be performed at atmospheric and super-atmospheric pressures.

The following examples are included for illustrative purposes only and do not limit the scope of the invention or claims. Unless otherwise stated, all parts and percentages are by weight.

EXAMPLE 1

To a stirred solution of 10 g of benzocyclobutene and 18.25 mL of chloromethyl methyl ether in 100 mL of methylene chloride at −78° C. under a nitrogen atmosphere, 11.1 g tin tetrachloride was added slowly over a period 1 hour and stirring was continued for 6 more hours at −78° C. The reaction mixture was then poured into an ice cold sodium hydroxide solution (10%) and extracted with ethyl acetate. The organic layer was washed with brine and dried over magnesium sulfate. Removal of the solvent followed by purification by flash chromatography afforded 6 g of 4-chloromethyl-benzocyclobutene (41%) as a colorless liquid.

NON-INVENTION COMPARATIVE EXAMPLE

Following the procedure for the chloromethylation of aromatic compounds as set forth in Fuson et al, *Organic Reactions*, Vol. 1, page 64–90, a mixture of benzocyclobutene and chloromethyl methyl ether was contacted with stannic tetrachloride catalyst. The reaction was carried out at 0° C. and worked up by adding to ice. Under these conditions, benzocyclobutene did not give the chloromethylated product. The reaction was also investigated using titanium tetrachloride and zinc chloride as catalysts. However, the expected product was not obtained in either case.

The data demonstrate the importance of effecting the chloromethylation reaction at temperatures not contemplated by the prior art and also demonstrate the specificity of tin (stannic) tetrachloride as the chloromethylation catalyst.

The above description is considered that of the preferred embodiment only. Modifications of the invention will occur to those who make or use the invention. Therefore, it is understood that the embodiment described above is merely for illustrative purposes and is not intended to limit the scope of the invention, which is defined by the following claims as interpreted according to the principles of patent law, including the doctrine of equivalence.

The embodiments of the invention in which an exclusive property or privilege is claimed are defined as follows:

1. A process for chloromethylating an arylcyclobutene compound which comprises reacting at a temperature in the range of about −120° C. to about −40° C. at least one butene compound with an excess of chloromethyl methyl ether in the presence of a catalytic amount of stannic chloride and neutralizing the resulting chloromethylarylcyclobutene with an effective amount of at least one neutralization agent at a temperature in the range of about −80° C. to about −70° C.

2. A process in accordance with claim 1 wherein arylcyclobutene compound comprises benzocyclobutene 3. A process in accordance with claim 1 wherein said neutralization agent comprises sodium hydroxide.

4. A process in accordance with claim 3 wherein said sodium hydroxide is cooled to a temperature of at least 0 C prior to its admixture with the chloromethylarylcyclobutene.

5. A process in accordance with claim 2 wherein the amount of stannic chloride is about 0.5 mol/mol arylcyclobutene.

6. A process in accordance with claim 5 wherein said reaction temperature is in the range from about −80° C. to about −70° C.

7. A process in accordance with claim 6 wherein said neutralization agent comprises sodium hydroxide.

8. A process in accordance with claim 7 wherein said sodium hydroxide is cooled to a temperature of at least 0° C. prior to its admixture with the chloromethylbenzocyclobutene.

9. A process in accordance with claim 8 wherein said neutralization is effected at a temperature in the range from about −80° C. to about −70° C.

10. A process in accordance with claim 1 wherein said arylcyclobutene compound has the formula:

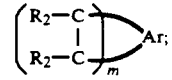

wherein Ar is an aryl moiety; R is separately and independently in each occurrence hydrogen, an electron-donating moiety, or an electron-withdrawing moiety; and m is an integer of at least 1.

11. A process in accordance with claim 10 wherein said reaction temperature is in the range from about −80° C. to about −70° C.

12. A process in accordance with claim 11 wherein said neutralization agent is cooled to a temperature of at least 0° C. prior to its admixture with the chloromethylarylcyclobutene.

13. A process in accordance with claim 12 wherein said neutralization is effected at a temperature in the range from about −80° C. to about −70° C.

14. A process in accordance with claim 11 wherein said neutralization agent comprises sodium hydroxide.

15. A process in accordance with claim 14 wherein said sodium hydroxide is cooled to a temperature of at least 0° C. prior to its admixture with the chloromethylarylcyclobutene.

16. A process in accordance with claim 15 wherein said neutralization is effected at a temperature in the range of about −80° C. to about −70° C.

17. A process in accordance with claim 16 wherein said arylcyclobutene comprises benzocyclobutene and said chloromethylarylcyclobutene comprises 3-chloromethyl benzocyclobutene.

* * * * *

UNITED STATES PATENT AND TRADEMARK OFFICE
CERTIFICATE OF CORRECTION

PATENT NO. : 5,099,083
DATED : March 24, 1992
INVENTOR(S) : P. J. Thomas and R. Garth Pews, both of Midland, Mich.

It is certified that error appears in the above-identified patent and that said Letters Patent is hereby corrected as shown below:

Title page, item [54], and col. 1, lines 1 - 2
" PROCESS FOR PREPARING 3-CHLOROMETHYLBENZO-CYCLOBUTENE "
should read
-- PROCESS FOR PREPARING 3-CHLOROMETHYLBENZOCYCLOBUTENE --.

Column 5, line 65, delete " one butene " and insert -- one arylcyclobutene --.

Column 6, line 13, delete " 0 C " and insert -- 0°C --.

Signed and Sealed this

Twenty-second Day of June, 1993

Attest:

MICHAEL K. KIRK

Attesting Officer  Acting Commissioner of Patents and Trademarks